United States Patent
Leung et al.

(10) Patent No.: US 9,597,299 B2
(45) Date of Patent: Mar. 21, 2017

(54) METHOD FOR TREATING GEFITINIB-RESISTANT NON-SMALL-CELL LUNG CANCER

(71) Applicant: Macau University of Science and Technology, Macao (MO)

(72) Inventors: Lai-Han Leung, Macao (MO); Xing-Xing Fan, Macao (MO); Liang Liu, Macao (MO); Zebo Jiang, Macao (MO)

(73) Assignee: Macau University of Science and Technology, Macau (MO)

( * ) Notice: Subject to any disclaimer, the term of this patent is extended or adjusted under 35 U.S.C. 154(b) by 0 days.

(21) Appl. No.: 14/624,574

(22) Filed: Feb. 17, 2015

(65) Prior Publication Data

US 2016/0158163 A1  Jun. 9, 2016

Related U.S. Application Data (60) Provisional application No. 62/087,216, filed on Dec. 3, 2014.

(51) Int. Cl.
*A61K 31/661* (2006.01)
*A61K 31/09* (2006.01)

(52) U.S. Cl.
CPC ................... *A61K 31/09* (2013.01)

(58) Field of Classification Search
CPC .................................................. A61K 31/661
USPC ......................................................... 514/717
See application file for complete search history.

(56) References Cited

U.S. PATENT DOCUMENTS 7,384,925 B2 *  6/2008  Chaplin .................. C07C 43/23
                                                        514/114

OTHER PUBLICATIONS

Raul, Oxidative Stress and Disease (2006), 20(Resveratrol in Health and Disease), 385-398.*
Gansler, T., et al., Sixty years of CA: a cancer journal for clinicians. CA: a cancer journal for clinicians, 2010. 60(6): p. 345-50.
Chang, A., Chemotherapy, chemoresistance and the changing treatment landscape for NSCLC. Lung cancer, 2011. 71(1): p. 3-10.
Tam, I.Y., et al., Double EGFR mutants containing rare EGFR mutant types show reduced in vitro response to gefitinib compared with common activating missense mutations. Molecular cancer therapeutics, 2009. 8(8): p. 2142-51.

(Continued)

*Primary Examiner* — San-Ming Hui
(74) *Attorney, Agent, or Firm* — Spruson & Ferguson (Hong Kong) Limited; Sam T. Yip (57) ABSTRACT

The present invention relates to a method for treating gefitinib-resistant non-small-cell lung cancer (NSCLC) comprising administering an effective amount of a resveratrol analog, (Z)3,4,5,4'-tetramethoxystilbene (TMS), to a subject in need thereof. The present invention also relates to a method for inducing apoptosis in gefitinib-resistant NSCLC cells comprising contacting the resveratrol analog to the cells at an effective amount. The present methods are mediated by different signaling pathways connected to cell proliferation and differentiation such as mTOR, JNK, and certain EGFR phosphorylated tyrosine kinase.

15 Claims, 7 Drawing Sheets

(56) References Cited

OTHER PUBLICATIONS

Leung, E.L., et al., SRC promotes survival and invasion of lung cancers with epidermal growth factor receptor abnormalities and is a potential candidate for molecular-targeted therapy. Molecular cancer research : MCR, 2009. 7 (6): p. 923-32.

Wong, D.W., et al., The EML4-ALK fusion gene is involved in various histologic types of lung cancers from nonsmokers with wild-type EGFR and KRAS. Cancer, 2009. 115(8): p. 1723-33.

Jun, H.J., et al., The oncogenic lung cancer fusion kinase CD74-Ros activates a novel invasiveness pathway through E-Syt1 phosphorylation. Cancer research, 2012. 72(15): p. 3764-74.

Ono, M. and M. Kuwano, Molecular mechanisms of epidermal growth factor receptor (EGFR) activation and response to gefitinib and other EGFR-targeting drugs. Clinical cancer research : an official journal of the American Association for Cancer Research, 2006. 12(24): p. 7242-51.

Niu, X., et al., The anti-inflammatory effects of sanguinarine and its modulation of inflammatory mediators from peritoneal macrophages. European journal of pharmacology, 2012. 689(1-3): p. 262-9.

Catalgol, B., et al., Resveratrol: French paradox revisited. Frontiers in pharmacology, 2012. 3: p. 141.

Pearson, K.J., et al., Resveratrol delays age-related deterioration and mimics transcriptional aspects of dietary restriction without extending life span. Cell metabolism, 2008. 8(2): p. 157-68.

Hua, J. et al., inhibits pathologic retinal neovascularization in Vldlr(-/-) mice. Investigative ophthalmology & visual science, 2011. 52(5): p. 2809-16.

Baur, J.A., et al., Resveratrol improves health and survival of mice on a high-calorie diet. Nature, 2006. 444(7117): p. 337-42.

Luo, H., et al., Resveratrol induces premature senescence in lung cancer cells via ROS-mediated DNA damage. PloS one, 2013. 8(3): p. e60065.

Ma, Z., et al., Resveratrol analog trans 3,4,5,4'-tetramethoxystilbene (DMU-212) mediates anti-tumor effects via mechanism different from that of resveratrol. Cancer chemotherapy and pharmacology, 2008. 63(1): p. 27-35.

Androutsopoulos, V.P., et al., Anticancer effects of the metabolic products of the resveratrol analogue, DMU-212: structural requirements for potency. European journal of medicinal chemistry, 2011. 46(6): p. 2586-95.

\* cited by examiner

METHOD FOR TREATING GEFITINIB-RESISTANT NON-SMALL-CELL LUNG CANCER

CROSS REFERENCE TO RELATED APPLICATION

Pursuant to 35 U.S.C. §119(e), this is a non-provisional patent application which claims benefit from U.S. provisional patent application Ser. No. 62/087,216 filed Dec. 3, 2014, and the disclosure of which is incorporated herein by reference in its entirety.

COPYRIGHT NOTICE

A portion of the disclosure of this patent document contains material, which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

TECHNICAL FIELD

The present invention provides a method for treating Gefitinib-resistant non-small-cell lung cancer (NSCLC). More specifically, the present invention provides a method for treating NSCLC comprising administering an effective amount of resveratrol analogue to a subject in need thereof.

BACKGROUND OF THE INVENTION

Lung cancer is the leading cause of cancer deaths globally [1]. Patients with NSCLC, which accounts for over 80% of all the lung cancer cases, are often diagnosed at advanced stages of the disease, thus the prognosis of lung cancer remains poor [2]. With the development of advanced gene sequencing technology, the therapeutic strategy of NSCLC has been modified towards personalized therapy. Some specific driver genetic mutations have been identified in NSCLC, such as EGFR [3, 4], EML4-ALK fusion gene [5] and ROS fusion gene [6], which directs the development of molecular-targeted drug discovery of pharmaceutical industry and therapy for individual NSCLC patients. For example, gefitinib, which is also known as tyrosine kinase inhibitor (TKI), specifically inhibits EGFR and its downstream survival signaling pathway [7]. However, despite the initial significant responses to gefitinib treatment, like other chemotherapeutic agents, patients acquire resistance to gefitinib ultimately, and the median time to disease progression is just about 12 months [8]. Although the reason of drug resistance behind might be various, 49% of the resistance cases are associated with double mutations on EGFR L858R+T790M [8]. Therefore, there is an urgent need to identify EGFR crosstalk pathways and to discover more effective agents as candidate drugs for gefitinib-resistant NSCLC patients.

The investigation of 'French Paradox' which describes improved cardiovascular outcomes despite a high-fat diet in French people opens the study of resveratrol in many disorders and diseases [9-12]. Resveratrol is a polyphenol which wildly exists in grapes. It is a well-known chemopreventive and chemotherapeutic agent [13, 14]. The anticancer effect of resveratrol and its derivatives attracted mostly attentions. For example, DMU-212, a methoxylated trans-stilbene resveratrol analogue [15], has been testing in clinical trial. Many other derivatives and their use are still being investigated in lab.

SUMMARY OF THE INVENTION

Accordingly, the main objective of the present invention is to provide a method for treating gefitinib-resistant non-small-cell lung cancer (NSCLC) comprising administering an effective amount of resveratrol derivative, (Z)3,4,5,4'-tetramethoxystilbene (TMS), to a subject suffering from gefitinib-resistant non-small-cell lung cancer (NSCLC). In one embodiment, the effective amount of the TMS being administered to the subject in need thereof ranges from 40 nM to 80 nM within a 24-hour time course. In another embodiment, the effective amount of the TMS being administered to the subject in need thereof is 57.2 nM±13.5 nM.

Another objective of the present invention is to provide a method for inducing apoptosis in gefitinib-resistant NSCLC cells comprising contacting the resveratrol derivative, TMS, to the gefitinib-resistant NSCLC cells at an effective amount. In one embodiment, the effective amount of resveratrol derivative ranges between 40 nM and 80 nM within a 24-hour time course. In another embodiment, the effective amount is 57.2 nM±13.5 nM.

BRIEF DESCRIPTION OF THE DRAWINGS

Embodiments of the present invention are described in more detail hereinafter with reference to the drawings, in which.

DETAILED DESCRIPTION OF THE INVENTION

The following description and the corresponding embodiments of the present invention are set forth as preferred examples. It will be apparent to those skilled in the art that modifications, including additions and/or substitutions, may be made without departing from the scope and spirit of the invention. Specific details may be omitted so as not to obscure the invention; however, the disclosure is written to enable one skilled in the art to practice the teachings herein without undue experimentation.

Example 1

Cytotoxicity effect of TMS on gefitinib-resistant NSCLC cells and normal lung epithelial cells is demonstrated by the cell viability assay.

Figure 1:
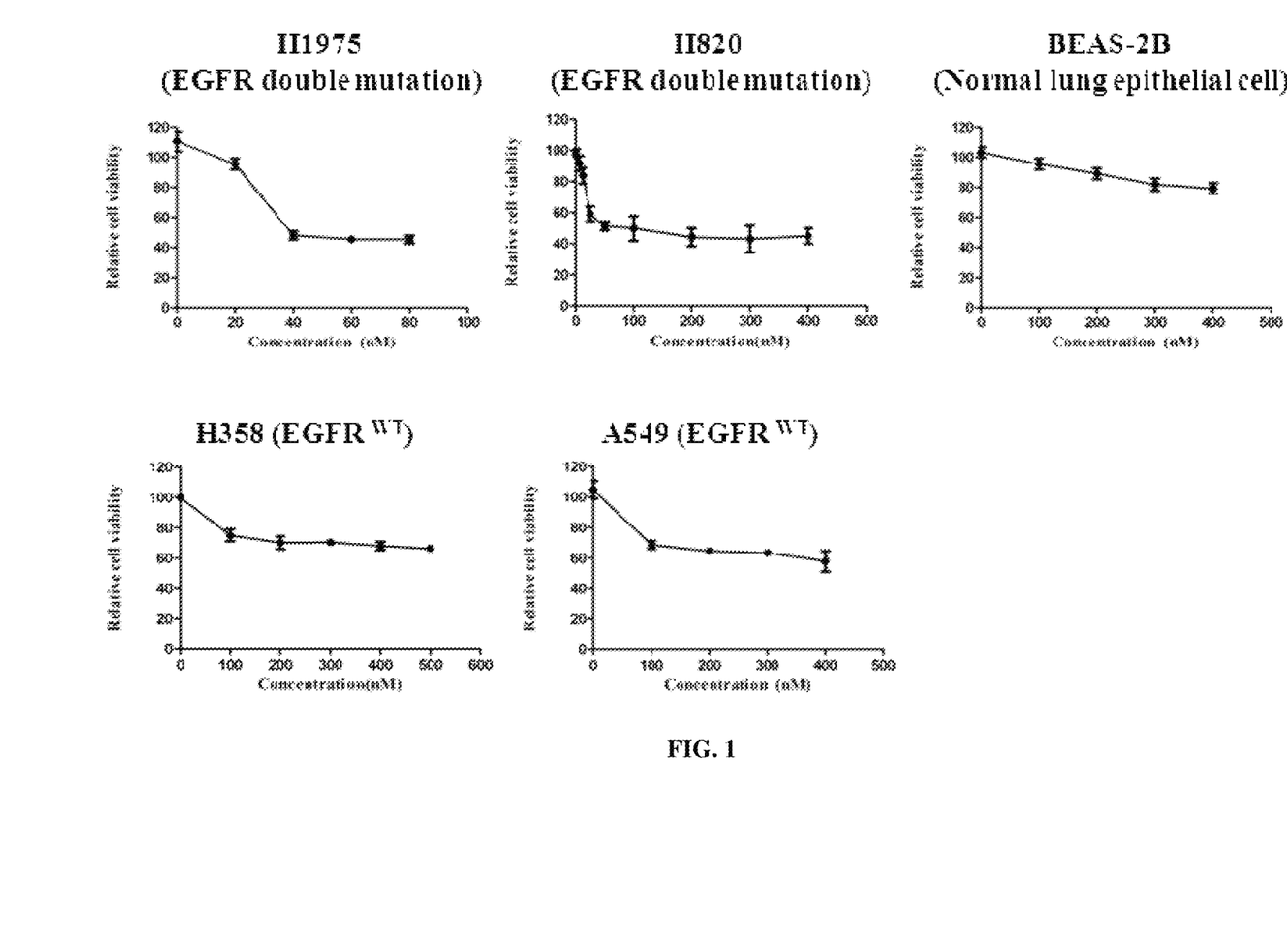
FIG. 1 shows the effect of different concentrations of TMS of the present invention on cell line H1975, H820 (gefitinib-resistant non-small-cell lung cancer cell line); A549, H358 (EGFR wild-type non-small-cell lung cancer cell line) and normal human bronchial epithelial cell (BEAS-2B) in terms of their viability.

In FIG. 1, TMS shows selectivity on gefitinib-resistant NSCLC cells (H1975 and H820 cell line), while there is a lower $IC_{50}$ on normal cells (BEAS-2B cell line) and other types of NSCLC cells such as A549 and H358 which are EGFR wild-type non-small-cell lung cancer cell lines. Table 1 summarizes the $IC_{50}$ values of five different cell lines treated with TMS.

TABLE 1

| Cell line | $IC_{50}$ Value |
|---|---|
| H1975 (EGFR double mutation) | 57.2 ± 13.5 nM |
| H820 (EGFR double mutation) | 135.5 ± 35.9 nM |
| A549 (EGFR wild-type) | >400 nM |
| H358 (EGFR wild-type) | >400 nM |
| BEAS-2B (normal epithelial cells) | >400 nM |

Example 2

Figure 2:
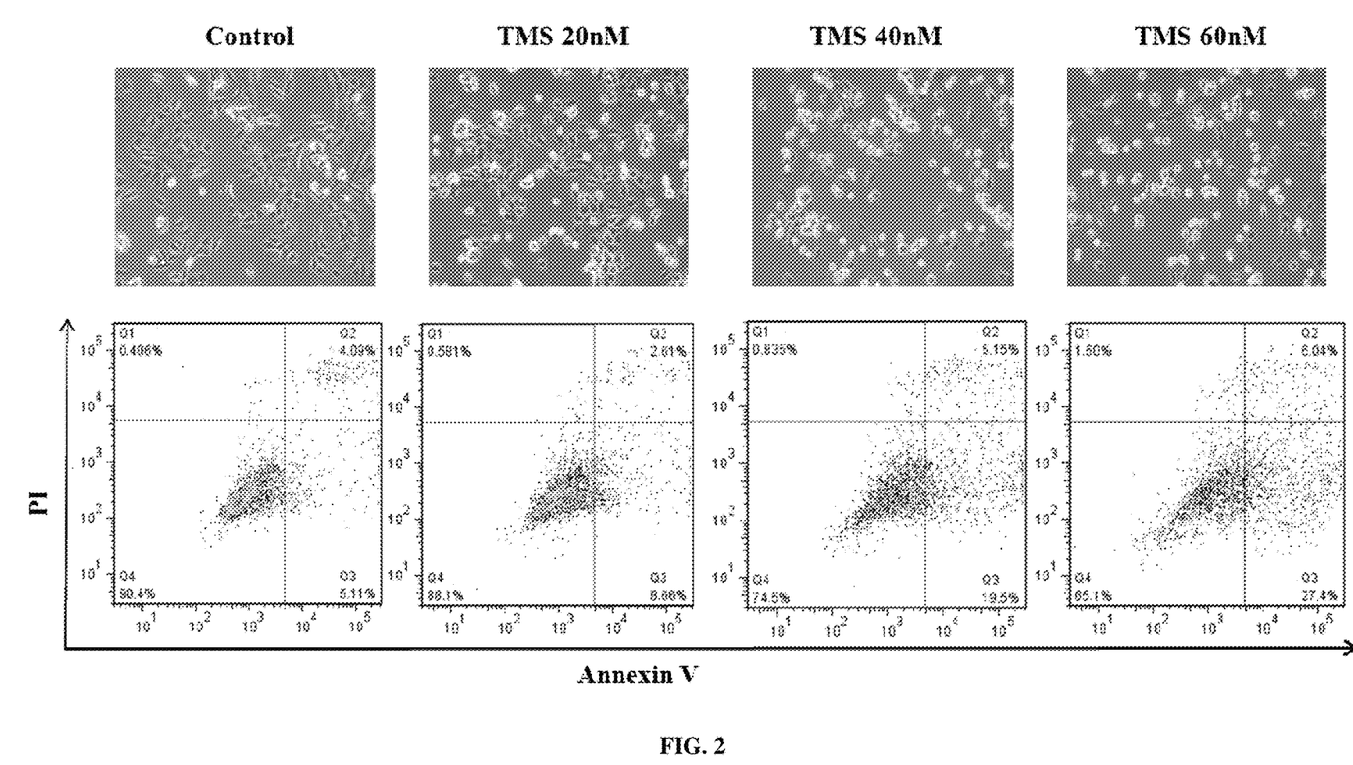
FIG. 2 shows the cell morphology under the microscope (upper panel) and flow cytometry result (lower panel) of cell line H1975 treated with different concentrations of TMS of the present invention.

FIG. 2 shows that TMS exerts anticancer effect through inducing apoptosis in gefinitib-resistant NSCLC cell lines.

Example 3

Figure 3:
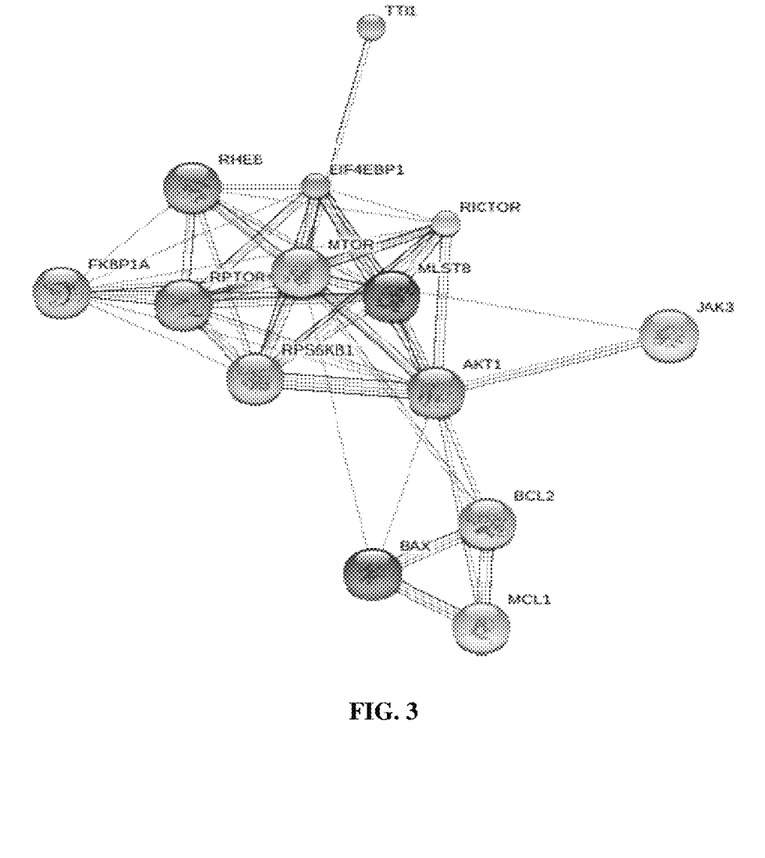
FIG. 3 is a schematic diagram showing the proteomic analysis result of TMS on different markers involved in apoptosis of gefitinib-resistant non-small-cell lung cancer cells.
Figure 4:
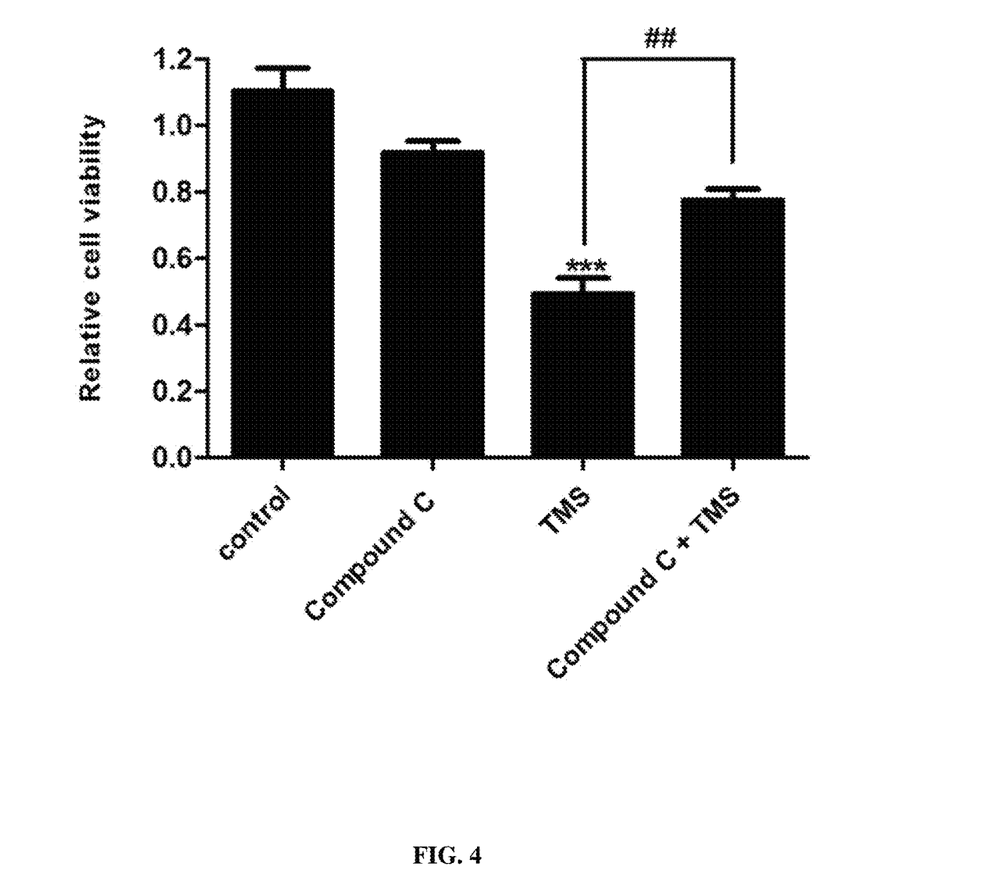
FIG. 4 shows the effect of different treatment groups (control; compound c; TMS alone; TMS+compound c) on cell line H1975 in terms of relative cell viability; ##: P<0.01; ***: P<0.001.

Proteomics analysis results in FIG. 3 show that mammalian target of rapamycin (mTOR) is significantly inhibited by TMS. Moreover, activation of mTOR pathway by compound c, where compound c is a well-known AMPK inhibitor, and AMPK is upstream of mTOR counteracts the effect of TMS, indicating that inhibition of mTOR is required for TMS to induce apoptosis in gefitinib-resistant NSCLC cells. Relative cell viability of gefitinib-resistant NSCLC cells under different treatments is shown in FIG. 4. TMS alone (40 nM) is the most effective in inducing apoptosis in gefitinib-resistant NSCLC cells among four different treatment groups in this example.

Example 4

Figure 5:
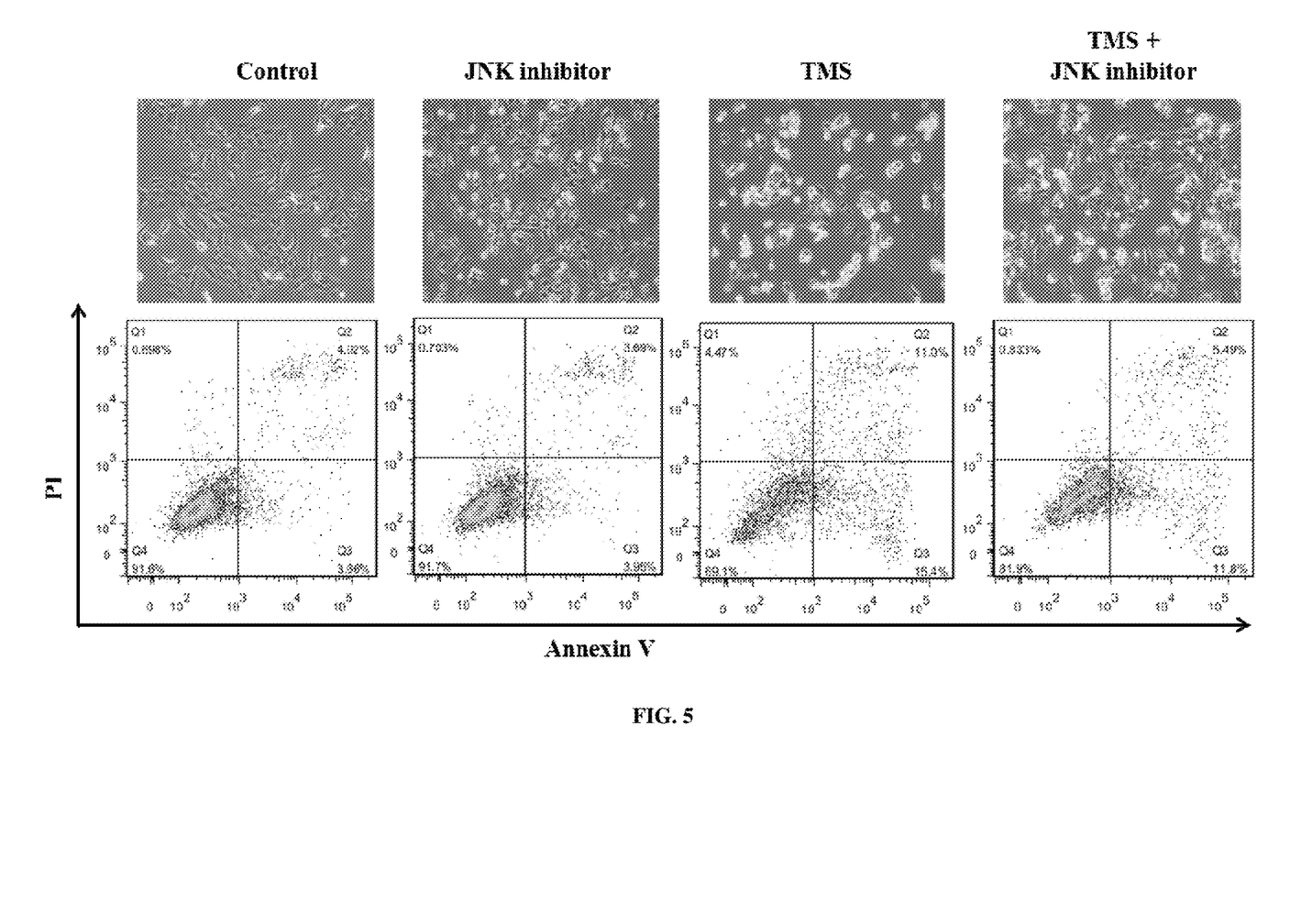
FIG. 5 shows the cell morphology under the microscope (upper panel) and flow cytometry result (lower panel) on cell line H1975 treated with different combination of compounds (control; 50 μM JNK inhibitor; 40 μM TMS; 50 μM JNK inhibitor+40 μM TMS).
Figure 6:
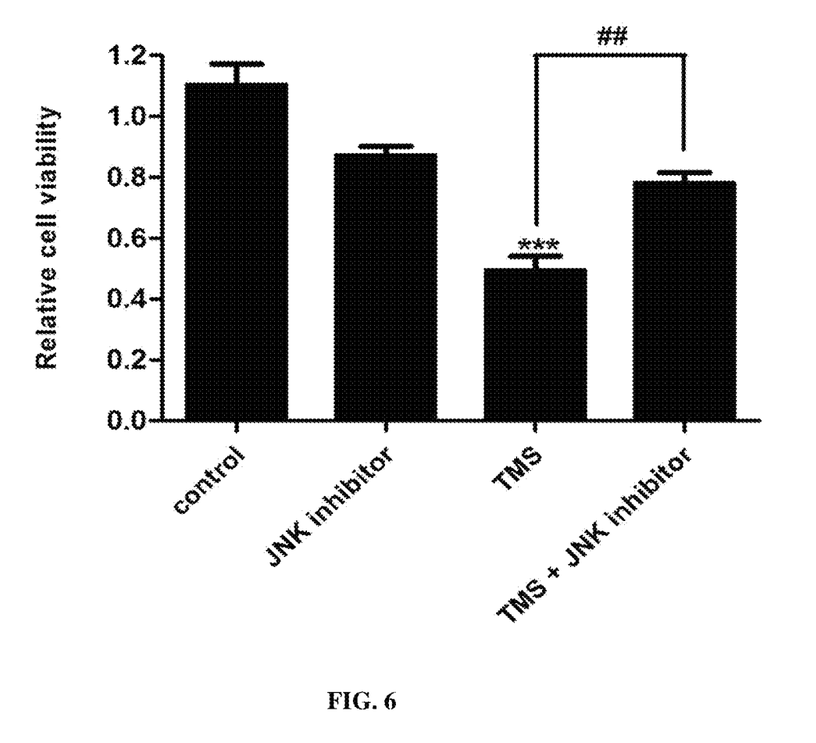
FIG. 6 shows the effect of different combination of compounds ((control; 50 μM JNK inhibitor; 40 μM TMS; 50 μM JNK inhibitor+40 μM TMS) on cell line H1975 in terms of relative cell viability; ##: P<0.01; ***: P<0.001.

FIG. 5 shows that treatment of JNK inhibitor significantly blocks the apoptosis and cell death induced by TMS, indicating that JNK activation is essential to TMS-induced apoptosis in gefitinib-resistant NSCLC cells. Again, TMS alone is the most effective in inducing apoptosis in gefitinib-resistant NSCLC cells among four different treatment groups, as shown in FIG. 6

Example 5

Figure 7:
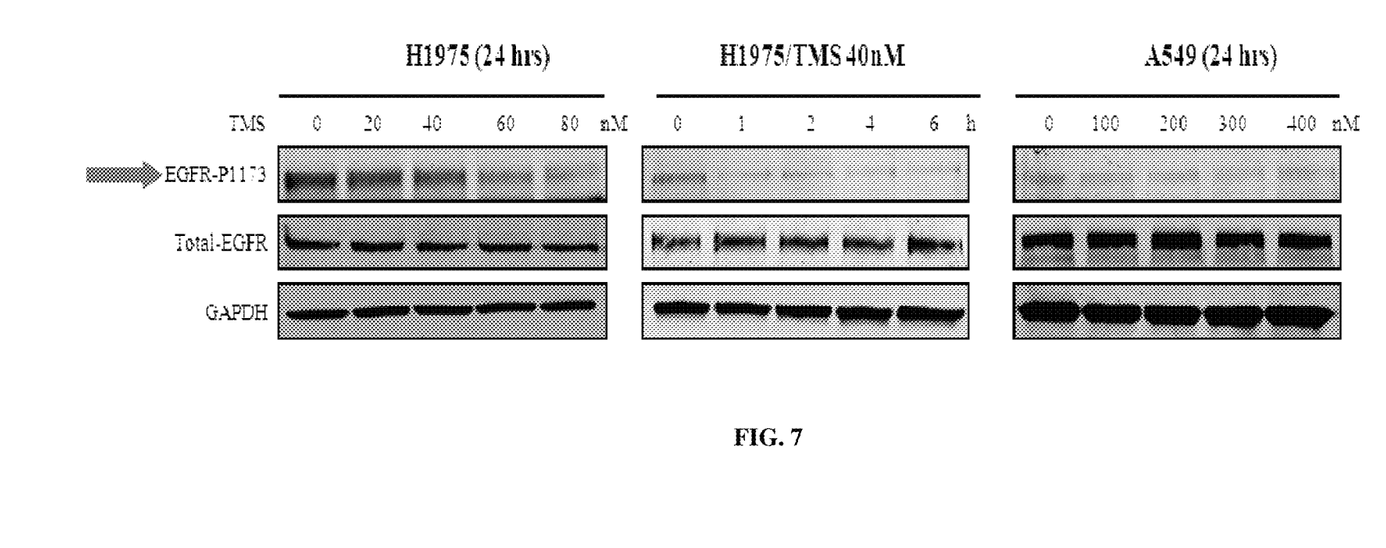
FIG. 7 shows the result of immunoblot analysis of H1975 (left and middle columns) and A549 (right column) cell lysate after being treated with different concentrations of TMS (left and right columns) and at different time points (middle column) with a fixed concentration of TMS; antibody against glyceraldehyde 3-phosphate dehydrogenase (GADPH) serves as loading control.

FIG. 7 shows that TMS inhibits the activation of EGFR PY1173 in gefitinib-resistant NSCLC cells, where EGFR PY1173 is an activation site of EGFR and can further activate the downstream effector STAT3 and STAT5, leading to an increase in cell proliferation. In this example, TMS at 40, 60 and 80 nM inhibits the activation of EGFR PY1173 in gefitinib-resistant NSCLC cells significantly. Moreover, the inhibition of PY1173 activation happens as early as in 1 hour after TMS treatment. Interestingly, this inhibitory effect of TMS on EGFR is not detected in A549 cells, suggesting that TMS is selective for killing NSCLC cells that have EGFR mutation and are resistant to current gefitinib treatment. Even we used 10-time higher concentration of TMS to treat A549, no suppression of EGFR PY1173 was observed, indicating TMS is more effective in inhibiting H1975.

INDUSTRIAL APPLICABILITY

The present invention is useful in developing into pharmaceutical composition for treating patients with gefitinib-resistant NSCLC which is difficult to treat by using the conventional therapies. The findings in the present invention also provide insight on developing specific and selective drug for gefitinib-resistant NSCLC.

The foregoing description of the present invention has been provided for the purposes of illustration and description. It is not intended to be exhaustive or to limit the invention to the precise forms disclosed. Many modifications and variations will be apparent to the practitioner skilled in the art.

The embodiments or examples are chosen and described in order to better explain the principles of the invention and its practical application, thereby enabling others skilled in the art to understand the invention for various embodiments and with various modifications that are suited to the particular use contemplated. It is intended that the scope of the invention be defined by the appended claims and their equivalence.

REFERENCE

The following references are also incorporated herein by reference in their entirety.
1. Gansler, T., et al., *Sixty years of CA: a cancer journal for clinicians*. CA: a cancer journal for clinicians, 2010. 60(6): p. 345-50.
2. Chang, A., *Chemotherapy, chemoresistance and the changing treatment landscape for NSCLC*. Lung cancer, 2011. 71(1): p. 3-10.
3. Tam, I. Y., et al., *Double EGFR mutants containing rare EGFR mutant types show reduced in vitro response to gefitinib compared with common activating missense mutations*. Molecular cancer therapeutics, 2009. 8(8): p. 2142-51.
4. Leung, E. L., et al., *SRC promotes survival and invasion of lung cancers with epidermal growth factor receptor abnormalities and is a potential candidate for molecular-targeted therapy*. Molecular cancer research: MCR, 2009. 7(6): p. 923-32.
5. Wong, D. W., et al., *The EML4-ALK fusion gene is involved in various histologic types of lung cancers from nonsmokers with wild-type EGFR and KRAS*. Cancer, 2009. 115(8): p. 1723-33.
6. Jun, H. J., et al., *The oncogenic lung cancer fusion kinase CD74-ROS activates a novel invasiveness pathway through E-Syt1 phosphorylation*. Cancer research, 2012. 72(15): p. 3764-74.
7. Ono, M. and M. Kuwano, *Molecular mechanisms of epidermal growth factor receptor (EGFR) activation and*

*response to gefitinib and other EGFR-targeting drugs.* Clinical cancer research: an official journal of the American Association for Cancer Research, 2006. 12(24): p. 7242-51.
8. Niu, X., et al., *The anti-inflammatory effects of sanguinarine and its modulation of inflammatory mediators from peritoneal macrophages.* European journal of pharmacology, 2012. 689(1-3): p. 262-9.
9. Catalgol, B., et al., *Resveratrol: French paradox revisited.* Frontiers in pharmacology, 2012. 3: p. 141.
10. Pearson, K. J., et al., *Resveratrol delays age-related deterioration and mimics transcriptional aspects of dietary restriction without extending life span.* Cell metabolism, 2008. 8(2): p. 157-68.
11. Hua, J., et al., *Resveratrol inhibits pathologic retinal neovascularization in Vldlr(-/-) mice.* Investigative ophthalmology & visual science, 2011. 52(5): p. 2809-16.
12. Baur, J. A., et al., *Resveratrol improves health and survival of mice on a high-calorie diet.* Nature, 2006. 444(7117): p. 337-42.
13. Luo, H., et al., *Resveratrol induces premature senescence in lung cancer cells via ROS-mediated DNA damage.* PloS one, 2013. 8(3): p. e60065.
14. Ma, Z., et al., *Resveratrol analog trans 3,4,5,4'-tetramethoxystilbene (DMU-212) mediates anti-tumor effects via mechanism different from that of resveratrol.* Cancer chemotherapy and pharmacology, 2008. 63(1): p. 27-35.
15. Androutsopoulos, V. P., et al., *Anticancer effects of the metabolic products of the resveratrol analogue, DMU-212: structural requirements for potency.* European journal of medicinal chemistry, 2011. 46(6): p. 2586-95.

What is claimed is:

1. A method for selectively treating gefitinib-resistant non-small-cell lung cancer (NSCLC) comprising administering an effective amount of (Z)3,4,5,4'-tetramethoxystilbene to a subject in need thereof to inhibit activation of epidermal growth factor receptor (EGFR) phosphorylated tyrosine kinase 1173 (PY1173).

2. The method of claim 1, wherein said effective amount is from 40 nM to 80 nM of the (Z)3,4,5,4'-tetramethoxystilbene.

3. The method of claim 2, wherein said effective amount is administered when the (Z)3,4,5,4'-tetramethoxystilbene contacts the gefitinib-resistant non-small-cell lung cancer cells.

4. The method of claim 3, wherein said effective amount is 57.2±13.5 nM.

5. The method of claim 1, wherein said administering the effective amount of said (Z)3,4,5,4'-tetramethoxystilbene to the subject in need thereof is mediated by activation of mTOR pathway.

6. The method of claim 1, wherein said administering the effective amount of said (Z)3,4,5,4'-tetramethoxystilbene to the subject in need thereof is mediated by JNK activation.

7. The method of claim 1, wherein said subject is human.

8. A method for selectively inducing apoptosis in gefitinib-resistant non-small-cell lung cancer (NSCLC) cells comprising contacting (Z)3,4,5,4'-tetramethoxystilbene to NSCLC cells at an effective amount to inhibit activation of epidermal growth factor receptor (EGFR) phosphorylated tyrosine kinase 1173 (PY1173).

9. The method of claim 8, wherein said effective amount is from 40 nM to 80 nM of the (Z)3,4,5,4'-tetramethoxystilbene.

10. The method of claim 8, wherein said effective amount is 57.2±13.5 nM.

11. The method of claim 8, wherein said contacting of the (Z)3,4,5,4'-tetramethoxystilbene to the gefitinib-resistant NSCLC cells at the effective amount is mediated by activation of mTOR pathway.

12. The method of claim 8, wherein said contacting of the (Z)3,4,5,4'-tetramethoxystilbene to the gefitinib-resistant NSCLC cells at the effective amount is mediated by JNK activation.

13. The method of claim 8, wherein said gefitinib-resistant NSCLC cells are of human origin.

14. The method of claim 1, wherein said gefitinib-resistant NSCLC has double mutation on said EGFR.

15. The method of claim 1, wherein said gefitinib-resistant NSCLC cells have double mutation on said EGFR.

* * * * *